(12) United States Patent
Kauffman et al.

(10) Patent No.: US 10,274,431 B1
(45) Date of Patent: Apr. 30, 2019

(54) METHOD OF EVALUATING PH USING AN INORGANIC-OXIDE NANOPARTICLE BASED OPTICAL PH SENSOR

(71) Applicant: Energy, United States Department of, Washington, DC (US)

(72) Inventors: Douglas Kauffman, Pittsburgh, PA (US); Christopher Matranga, Pittsburgh, PA (US); Paul R. Ohodnicki, Jr., Allison Park, PA (US); Xin Su, Wood-Ridge, NJ (US); Congjun Wang, Bethel Park, PA (US)

(73) Assignee: U.S. Department of Energy, Washington, DC (US)

( * ) Notice: Subject to any disclaimer, the term of this patent is extended or adjusted under 35 U.S.C. 154(b) by 302 days.

(21) Appl. No.: 15/098,714

(22) Filed: Apr. 14, 2016

Related U.S. Application Data

(60) Provisional application No. 62/147,235, filed on Apr. 14, 2015.

(51) Int. Cl.
  *G01N 21/77* (2006.01)
  *G01N 33/84* (2006.01)
  *G01N 31/22* (2006.01)

(52) U.S. Cl.
  CPC .......... *G01N 21/77* (2013.01); *G01N 21/7703* (2013.01); *G01N 33/84* (2013.01); *G01N 31/221* (2013.01)

(58) Field of Classification Search
  CPC ...... G01N 33/20; G01N 33/84; G01N 31/221; G01N 21/77; G01N 21/7703; Y10T 436/20

(Continued)

(56) References Cited

U.S. PATENT DOCUMENTS

| | | | |
|---|---|---|---|
| 8,638,440 B1* | 1/2014 | Ohodnicki, Jr. | G01N 21/783 356/437 |
| 2011/0207232 A1* | 8/2011 | Ostafin | B82Y 15/00 436/163 |

(Continued)

OTHER PUBLICATIONS

Wang et al. Nanoscale, vol. 7, Dec. 22, 2014, pp. 2527-2535.*
Ohodnicki, Jr. et al. Nanoscale, vol. 5, Jul. 30, 2013, pp. 9030-3039.*

*Primary Examiner* — Maureen Wallenhorst
(74) *Attorney, Agent, or Firm* — Timothy L. Harney; Jacob A. Heafner; Brian J. Lally

(57) ABSTRACT

A method for evaluating the pH of an aqueous solution by utilizing the optical properties of a pH sensing material includes optically active nanoparticles fixed to a substrate. The optically active nanoparticles have a localized refractive index modulation over a pH range from 2.0 to 12.0 of at least 1% and, where the plurality of optically active nanoparticles have an average nanoparticle diameter of less than about 500 nanometers. The method includes contacting the pH sensing material with the aqueous solution, illuminating the pH sensing material, and monitoring an optical signal generated through comparison of incident light and exiting light to determine the optical transmission, absorption, reflection, and/or scattering of the pH sensitive material. The optical signal of the pH sensitive material varies in response to the pH of the aqueous solution, providing a means by which the pH and any changes in the pH may be analyzed.

21 Claims, 11 Drawing Sheets

(58) Field of Classification Search
USPC ........ 436/25, 28, 72, 73, 75, 77, 80, 81, 83, 436/84, 127, 163, 164, 171; 422/82.05, 422/82.09, 82.11
See application file for complete search history.

(56) References Cited

U.S. PATENT DOCUMENTS

2013/0210156 A1* 8/2013 Wooley .............. A61B 5/14539
436/63
2014/0318990 A1* 10/2014 Star ........................ B82Y 15/00
205/787.5

* cited by examiner

METHOD OF EVALUATING PH USING AN INORGANIC-OXIDE NANOPARTICLE BASED OPTICAL PH SENSOR

RELATION TO OTHER APPLICATIONS

The present patent application claims priority to U.S. Provisional Patent No. 62/147,235 filed Apr. 14, 2015, and entitled "Harsh Environment Stable Oxide and Metal/Oxide Core Shell Particles for In-Situ pH Sensing and Measurements in Aqueous Environments," the contents of which are hereby incorporated by reference.

GOVERNMENT INTERESTS

The United States Government has rights in this invention pursuant to the employer-employee relationship of the Government to the inventors as U.S. Department of Energy employees and site-support contractors at the National Energy Technology Laboratory.

FIELD OF THE INVENTION

One or more embodiments relates to a method for sensing the pH of an aqueous solution through evaluation of the optical signal of a pH sensing material comprising optically active nanoparticles where the optically active nanoparticles comprise an inorganic oxide, have a localized refractive index modulation, and are fixed to a substrate.

BACKGROUND

Monitoring of chemical composition in harsh environments including downhole and underwater conditions is critically important for a range of fossil energy related applications, which include unconventional, deep and ultra-deep oil and gas resource recovery through drilling and hydraulic fracturing techniques, as well as environmental monitoring in reservoirs for $CO_2$ sequestration. These conditions represent extremely challenging environments for the development and deployment of sensing technologies due to an aggressive combination of temperature and pressure, as well as the presence of chemically corrosive chemical species and a potentially high salinity. Temperatures ranging up to 300° C. and pressures ranging up to 30,000 psi can be relevant for these applications depending on the specific environment. Such temperatures and pressures are beyond the limit of most electrical and electronic components used in sensor applications, due in many cases to the instabilities associated with packaging, wires, and interconnects. For this reason, approaches that eliminate the need for electrical components and connections at the sensing location can also eliminate a common mode of failure for conventional sensor devices.

Optical based sensing methodologies offer this advantage and can also be advantageous from a safety perspective in the presence of potentially flammable gas and chemical species. In particular, sensors that employ fiber-bragg gratings inscribed into specialty optical fibers capable of withstanding the temperature and pressure conditions of interest have already been deployed commercially for distributed pressure and temperature sensing. In contrast, optical fiber based sensors for subsurface chemical sensing applications have not been commercially deployed due in part to the lack of optical sensor elements with useful, reversible, and rapid responses to particular chemical species of interest.

While a broad range of parameters related to the chemistry of harsh conditions such as downhole conditions can be potentially monitored, pH is a key parameter whose accurate measurement at downhole wellbore conditions is critical in understanding formation fluid water chemistry to predict corrosion and scale potential. Because gases and solids can come out of solution as downhole samples are transported to surface laboratories, it is important to develop technologies for accurate pH measurements downhole in the native condition at reservoir temperatures and pressures. The lack of a robust measurement requires large safety margins in the selection of corrosion resistant materials and a significant economic impact can therefore be realized by the development of such a technology. In addition, measured pH values can be utilized to infer additional information about the chemical composition of a fluid such as the concentration of $CO_2$ in fluids contained within geological formations for $CO_2$ sequestration.

A broad range of technologies exist for pH sensing in aqueous conditions including pH sensitive dyes, electrochemical and potentiometric based approaches, and electronically conductive polyaniline-based polymers. Additionally, plasmonic sensors have been demonstrated in which noble metals are functionalized with capping agents or an organic matrix that mediates a response to pH through relatively large changes in swelling of the polymer, modification of refractive index or through protonation/deprotonation reactions, or aggregation and de-aggregation of particles in solution. See e.g. Mishra et al., "Surface plasmon resonance based fiber optic pH sensor utilizing Ag/ITO/Al/hydrogel layers," *Analyst* 9 (2013); see also Singh et al., "Fabrication and characterization of a highly sensitive surface plasmon resonance based fiber optic pH sensor utilizing high index layer and smart hydrogel," *Sensors and Actuators B* 173 (2012); see also Asian et al, "Enhanced Ratiometric pH Sensing Using SNAFL-2 on Silver Island Films: Metal-enhanced Fluorescence Sensing," *Journal of Fluorescence* 15(1) (2005); see also Toh et al, "Induced pH-dependent shift by local surface plasmon resonance in functionalized gold nanorods," *Nanoscale Research Letters* 8 (2013). Optical sensors based on protonation of silica-based sol-gel materials have also been reported. See Rayss t al., "Ion adsorption in the porous sol-gel silica layer in the fibre optic pH sensor," *Sensors and Actuators B* 87 (2002); and see Rayss et al., "Optical Aspects of Na+ Ions Adsorption on Sol-Gel Porous Films Used in Optical Fiber Sensors," *Journal of Colloid and Interface Science* 250 (2002). However, these silica gel materials required coating on a highly bent optical fiber to be effective which is undesirable for pH sensing applications due to limitations in sensor design including distributed interrogation. Similarly, the silica gels were utilized for pH sensing without a high temperature pretreatment significantly above the subsequent temperature at which sensing experiments are performed, which thereby would limit the stability of the silica gel sensing material to near-ambient temperature applications to avoid modifications to the silica based layer during the sensing experiment. Further, pH detectors which have previously incorporated optically active nanomaterials rely a supporting matrix where the matrix itself exhibits a change in surface charge density over a given pH range.

It would be advantageous if a measurement methodology allowed for mapping of information about pH in real-time spatially within harsh conditions such as wellbores and throughout geological formations. It would also be advantageous if the sensing approach was optical-based in nature with a sensing response that was not dependent upon protonation and deprotonation of an organic indicator dye, due to inherent limitations in both temperature stability and resistance to leaching. Higher stability sensing materials are desired for long-term operation in aggressive downhole environments. As such, it would be preferred to use alternative sensing materials that exhibit chemical and temperature stability but demonstrate a reversible response to changing pH conditions.

Provided herein is a method of pH sensing which addresses these weaknesses by exploiting the optical property changes of inorganic oxide based nanoparticles that are stable under harsh conditions. The method exhibits a strong overall optical response associated with reversible interactions between the pH sensing material and the solution for which pH is being monitored. Exploitation of the inorganic oxide based nanoparticles as the absorption-based indicator elements to replace organic dyes potentially allows for a broader application space, improved temperature stability, and the possibility of multi-parameter monitoring through broadband wavelength interrogation by monitoring changes in optical properties in response to other important parameters such as temperature. The application of nanoparticle based oxides also allows for modifying the corresponding wavelength dependence and magnitude of the optical response through tailoring particle size and shape. In some embodiments, optically active elements can be incorporated within the inorganic oxide nanoparticles having characteristic optical properties such as metal nanoparticles to form so-called core-shell nanoparticle structures.

These and other objects, aspects, and advantages of the present disclosure will become better understood with reference to the accompanying description and claims.

SUMMARY

The disclosure provides a method for evaluating the pH of an aqueous solution by utilizing the optical properties of a particular pH sensing material. The pH sensing material is comprised of a plurality of inorganic oxide-based optically active nanoparticles. The optically active nanoparticles have a localized refractive index modulation over a pH range from 2.0 to 12.0 of at least 1%, and generally have an average nanoparticle diameter of less than about 500 nanometers. The optically active nanoparticles are also affixed onto a substrate or onto suitable optical waveguide structures such as an optical fiber to avoid significant nanoparticle agglomeration with modulations in average interparticle spacing between adjacent nanoparticles being less than 10% and more preferably less than 1% as the pH of a solution phase is varied from 2.0 to 12.0.

The method generally comprises contacting the pH sensing material and the aqueous solution, illuminating the pH sensing material, and monitoring an optical signal. The optical signal is generated by illuminating the pH sensitive material with incident light from a light source and collecting the exiting light, and comparing the incident light and the exiting light in order to determine the optical transmission, absorption, reflection, and/or scattering of the pH sensitive material, without reliance on a supporting matrix material which exhibits a change in surface charge density over a pH range. The pH sensing material is responsive at least to some degree to the incident light at wavelengths corresponding to the optical signal. The strong optical response of the pH sensing materials disclosed is generally associated with the inorganic oxide-based optically active nanoparticles of the pH sensing material. Thus, the optical signal of the pH sensitive material varies in response to the pH of the aqueous solution, providing a means by which the pH and any changes in the pH may be analyzed. In a particular embodiment, the pH sensing material is illuminated by a wave propagating along a waveguide, such as a fiber optic cable.

The basic principles of one example of the method are illustrated at FIG. 1. At FIG. 1, light from light source 102 is directed along an optical fiber 104 and focused by lens 105 producing incident light 106 illuminating pH sensing material 101. The pH sensing material 101 is in contact with an aqueous solution S. Concurrently, exiting light 107 is collected behind a specimen using a probe 108 in communication with a spectrophotometer 109. Data generated by spectrophotometer 109 or supporting equipment is processed, and an optical signal is displayed. The optical signal is a comparison of the incident light and the exiting light and indicates the absorption, transmission, reflection, and scattering of the incident light at certain wavelengths by pH sensing material 101. The optical signal indicates selective photon absorption or scattering of light at certain wavelengths by pH sensing material 101. Accordingly, incident light 106, exiting light 107, and pH sensing material 101 generate an optical signal which depends on the pH of the aqueous solution S, and the optical signal at monitored wavelengths is indicative of the pH and any changes in the pH.

An additional embodiment is depicted at FIG. 2, where the pH sensing material 221 is illuminated by a wave propagating along a waveguide, such as a fiber optic cable. The waveguide is comprised of a core material 223 in contact with a cladding material 224, where core material 223 has a refractive index greater than cladding material 224. For example, core material 223 and cladding material 224 may be comprised of silica and various additions such as germanium, titanium, phosphorous, boron, fluorine, or other dopants in order to alter the respective refractive indices and meet the necessary criteria. At FIG. 2 light source 222 emits light into core material 223, generating wave 225 penetrating cladding material 224. Additionally at FIG. 2, pH sensing material 221 having the disclosed properties is placed in contact with core material 223 such that pH sensing material 221 is illuminated by wave 225 as incident light, as illustrated. Exiting light 226 is collected by probe 227, connected to spectrophotometer 228. Illumination of pH sensing material 221 by wave 226 enables evaluating the pH of aqueous solution S in contact with pH sensing material 221 by monitoring a shift in the optical signal, as earlier described. The optical power and penetration depth of wave 225 into cladding 224 and pH sensing material 201 can be described by Beer-Lambert law in many cases. See e.g., Dickinson et al., "Convergent, Self-Encoded Bead Sensor Arrays in the design of an Artificial Nose," *Anal. Chem.* 71 (1999), among others. As is similarly understood, the optical power coupled into the evanescent field may be improved by various methods such as bending, optimizing the relative refractive indices of the core and cladding, use of hollow fibers, and other methods. See e.g., Elosua et al., "Volatile Organic Compound Optical Fiber Sensors: A Review," *Sensors* 6 (2006), among others. However, responses that are substantially absent without fiber bending are typically less preferred due to limitations imposed upon optical fiber sensor design and deployment including an ability to perform distributed interrogation.

The optically active nanoparticles comprise an inorganic oxide. Exemplary inorganic oxide-based nanoparticles include silica, alumina, zirconia, rare-earth doped silica, yttria-stabilized zirconia, and others. Other exemplary inorganic oxide-based nanoparticles include electronically conductive inorganic metal oxides such as Al-doped ZnO (AZO), Sn-doped In2O3 (ITO), Nb-doped TiO2 (NTO), and others. In a further embodiment, the pH sensing material comprises metal-oxide/inorganic core-shell nanoparticles. Metal-oxide/inorganic core-shell nanoparticles are comprised of metals commonly referred to as noble or precious metals which tend to exhibit improved resistance to corrosion, reduced reactivity, and relatively high melting points such as gold, palladium, silver, platinum, ruthenium, rhodium, osmium, or iridium, or alloys or compounds thereof, at least partially surrounded by an inorganic oxide shell. The individual optically active nanoparticles in the plurality of optically active nanoparticles has a localized refractive index modulation over a pH range from 2.0 to 12.0 of at least 1%.

The novel process and principles of operation are further discussed in the following description.

DETAILED DESCRIPTION

Figure 1:
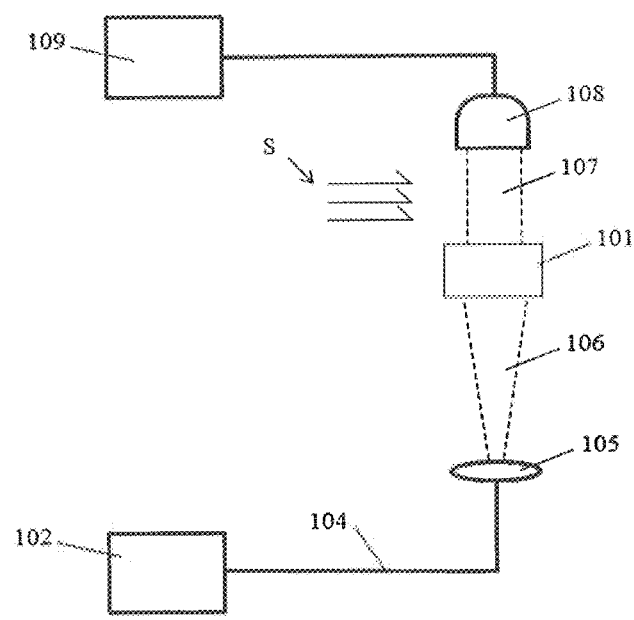
FIG. 1 illustrates an embodiment of the methodology.
Figure 2:
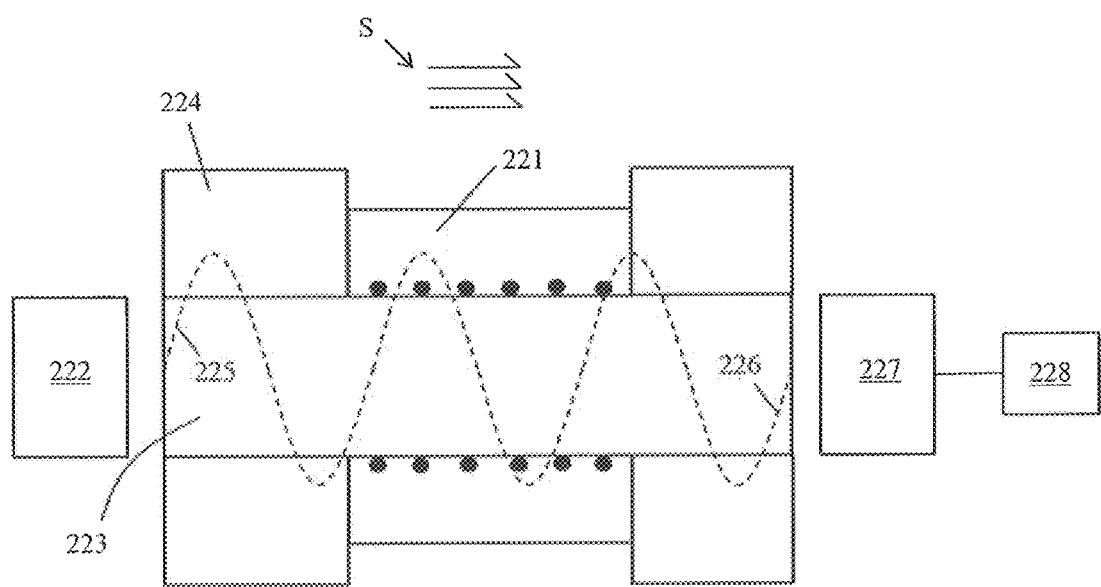
FIG. 2 illustrates another embodiment of the methodology.

The following description is provided to enable any person skilled in the art to use the invention and sets forth the best mode contemplated by the inventor for carrying out the invention. Various modifications, however, will remain readily apparent to those skilled in the art, since the principles of the present invention are defined herein specifically to provide a method of evaluating the pH of an aqueous solution based on changes to the optical properties of a pH sensing material comprised of optically active inorganic oxide based nanoparticles.

The disclosure provides a method for evaluating the pH of an aqueous solution by utilizing the optical properties of a particular pH sensing material. The pH sensing material is comprised of a plurality of inorganic oxide-based optically active nanoparticles fixed to a substrate. The optically active nanoparticles have a localized refractive index modulation over a pH range from 2.0 to 12.0 of at least 1%. Further, the optically active nanoparticles generally have an average nanoparticle diameter of less than about 500 nanometers. The optically active nanoparticles comprising the pH sensing material exhibit a modulation in interparticle spacing less than 10%. Preferably, the optically active nanoparticles comprising the pH sensing material exhibit a modulation in interparticle spacing less 1% over a pH range from 2.0 to 12.0. More preferably, the modulation in interparticle spacing is than 0.1% over a pH range from 2.0 to 12.0. The method generally comprises contacting the pH sensing material and the aqueous solution, illuminating the pH sensing material, and monitoring an optical signal. Contacting may be accomplished through immersing the pH sensing material in the aqueous solution as one would in a drilling bore hole, or filling with the aqueous solution a cuvette incorporating the pH sensing material. The optical signal is generated by illuminating the pH sensitive material with incident light from a light source and collecting the exiting light. Monitoring is performed by comparing the incident light and the exiting light in order to determine the optical transmission, absorption, reflection, and/or scattering of the pH sensitive material. The optical signal of the pH sensitive material varies in response to the pH of the aqueous solution, providing a means by which the pH and any changes in the pH may be analyzed.

As noted above, the optically active nanoparticles comprise an inorganic-oxide. In yet another embodiment, the optically active nanoparticles comprises an inorganic metal oxide of the formula $M_aO_b$. Exemplary inorganic oxide-based nanoparticles include silica, alumina, zirconia, rare-earth doped silica, yttria-stabilized zirconia, and others. In a further embodiment, the inorganic oxide-based nanoparticles are electronically conductive inorganic metal oxides such as Al-doped ZnO (AZO), Sn-doped In2O3 (ITO), Nb-doped TiO2 (NTO), and others. In a preferred embodiment, the inorganic oxide is a silica ($SiO_2$).

In a further embodiment, the pH sensing material comprises metal-oxide/core-shell nanoparticles. Metal-oxide/core-shell nanoparticles are comprised of metals commonly referred to as noble or precious metals which tend to exhibit improved resistance to corrosion, reduced reactivity, and relatively high melting points such as gold, palladium, silver, platinum, ruthenium, rhodium, osmium, or iridium, or alloys or compounds thereof, at least partially surrounded by an inorganic oxide shell. The individual optically active nanoparticles in the plurality of optically active nanoparticles has a localized refractive index modulation over a pH range from 2.0 to 12.0 of at least 1%. In one embodiment, the localized refractive index modulation is resultant from the inorganic-oxide shell's response to the pH of the aqueous solution. An exemplary inorganic oxide for the oxide shells of the pH sensing material comprising metal-oxide/core-shell nanoparticles is silica.

Figure 3:
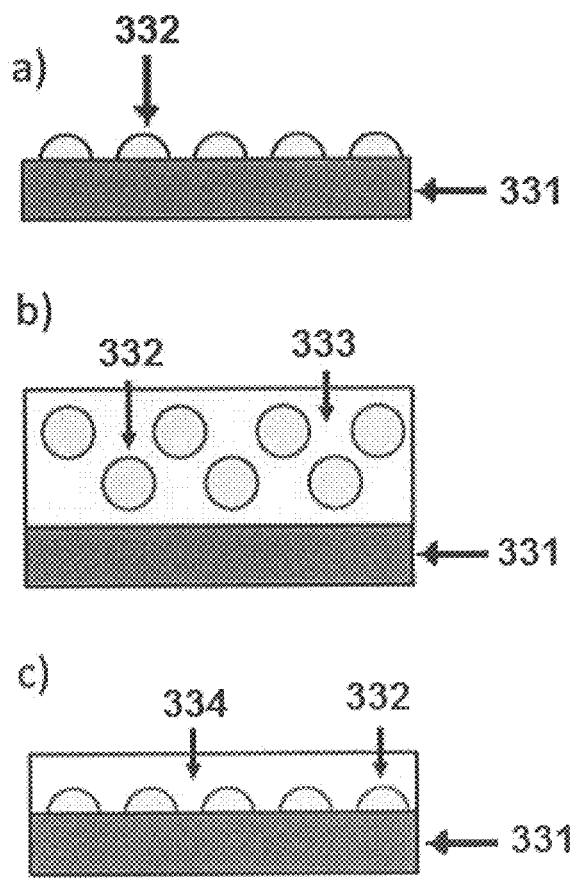
FIGS. 3(a)-(c) illustrate exemplary embodiments of the invention including the pH sensitive materials fixed to a substrate, fixed in a protective matrix, and fixed in a protective filter layer.

As illustrated in FIG. 3, the pH sensing material (particles) may be fixed to a substrate in several manners. Exemplary embodiments include as in FIG. 3a substrate 331, such as a planar glass substrate or an optical waveguide optical fiber is at least partially coated with the pH sensing materials 332, such that the pH sensing materials 332 are rigidly fixed directly to a substrate 331. In some embodiments the materials that comprise the pH sensing materials 332 and the substrate 331 may be the same, for example silica particles affixed on the surface of silica-based optical fibers, essentially a roughening of the silica surface layer. As depicted in FIG. 3b, the pH sensing materials 332 can be embedded in a solution permeable matrix phase 333 to immobilize and stabilize them in the conditions of interest as well as to tailor the overall optical response of the immobilized particles. The pH sensing materials 332 may be fixed to one or more underlayers that can be employed to improve adhesion and/or improve the overall optical response. Particles affixed directly to a substrate or underlayers can also be overcoated with a protective or filter layer that helps to stabilize, immobilize, and protect them or to prevent certain species or particulates in the solution from reaching the particles. In FIG. 3c, pH sensing materials 332 fixed directly to a substrate 331 or underlayers are shown substantially overcoated with a protective or filter layer 334 that helps to stabilize, immobilize, and protect them or to prevent certain species or particulates in the solution from reaching the particles.

As mentioned in reference to FIG. 3, in some embodiments, matrix and/or overlayers selected for use in the method are ion-selective filtering matrix and/or overlayers. The ion-selective filtering function of preferred matrix and/or overlayers (collectively matrix) can be important for reducing cross-sensitivity to other environmental parameters of interest related to ionic species and concentration present within the aqueous solution to be monitored. The optically active nanoparticles may be dispersed relatively uniformly or non-uniformly with respect materialist respective supporting material. In some cases, additional sensitive agents may also be incorporated into a matrix phase to enhance the response or to provide sensitivity to additional environmental parameters such as temperature. For example, rare earth ion dopants can impart a temperature dependent luminescence in a silica matrix. Similarly, the oxide-metal/core-shell particles such as Au/SiO2 are anticipated to have temperature dependent localized surface plasmon resonance absorption of the Au core.

The optically active nanoparticles have localized refractive index modulation over a pH range from 2.0 to 12.0 of at least 1%, in that across the pH range the optically active nanoparticles exhibit pH dependent optical response. Without being limited by theory, this localized refractive index modulation is typically thought to occur through the fact that inorganic oxide-based nanoparticles such as silica particles experience pH dependent surface charging in aqueous solutions. The formation of an electrical double layer at the charged surface effectively concentrates the ions to the porous silica leading to an increase in the effective refractive index of the inorganic oxide particles. The detailed dependence of surface charging behavior on solution phase pH can be sensitively dependent on the identity of the inorganic metal-oxide based nanoparticles as well as any functional groups on the surface. Because the refractive index modulation benefits from a porous inorganic metal-oxide based nanoparticle sensing material to allow for an effective modulation of the entire nanoparticle refractive index, in some preferred embodiments the inorganic metal-oxide based nanoparticles will have engineered nanoporosity. In addition to maximizing the effective index modulation of the optically active nanoparticles for given variation in pH, engineered nanoporosity may also allow for increased selectivity to pH relative to other solution phase parameters such as varying identity and concentration of ionic species. In some preferred embodiments, the identity of the inorganic metal-oxide based sensing layer will be selected and/or a surface functionalization will be performed to optimize the pH dependent surface charging behavior for a particular required pH dependent surface charging. In other preferred embodiments, the inorganic metal-oxide based sensing layers will be utilized in conjunction with an ion-selective membrane as a matrix or overlayer material to reduce the potential for cross-sensitivity to ionic species identity and concentration in the aqueous solution phase.

Figure 4:
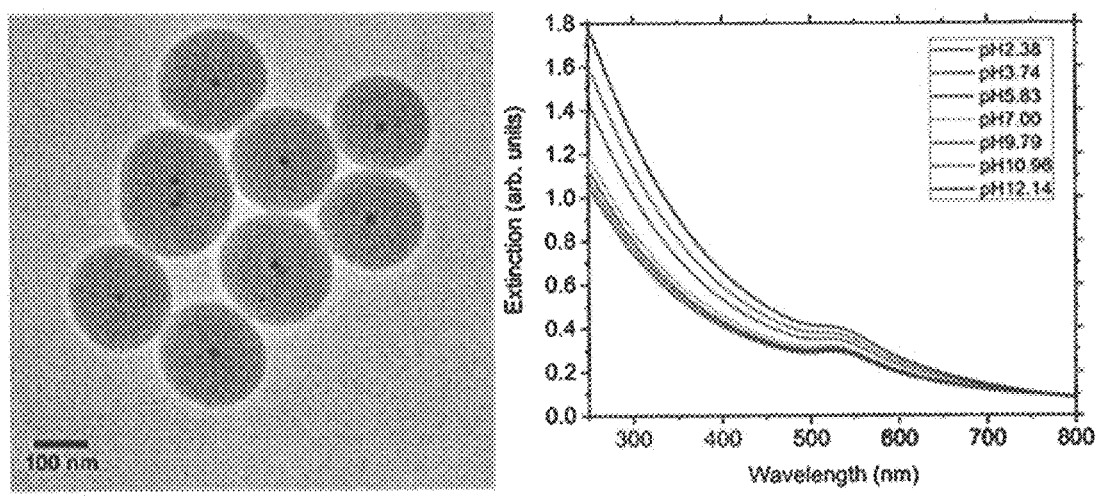
FIG. 4 illustrates a TEM image of gold/silica core/shell particles drop-cast onto a TEM and their corresponding extinction spectra measured in solution as a function of pH.

FIG. 4 illustrates exemplary pH dependent optical properties measured for optically active metal-oxide/core-shell nanoparticles dispersed within the solution phase. The metal-oxide/core-shell nanoparticles as shown in the TEM image of FIG. 4a show a strong pH dependence of the extinction spectra of the pH sensing material containing solution which is relatively stronger for basic solutions as seen in FIG. 4b. The pH dependence of the solution can have a dramatic impact on the extinction of light by the particles dispersed in solution. However, the extinction spectra for particles dispersed freely in solution can be sensitively dependent upon the level of aggregation which will be difficult to control and highly dependent upon the detailed chemistry of the aqueous solution phase to be interrogated. Hence, immobilized particles affixed on a substrate or optical waveguide structure are generally preferred for achieving reproducible and reversible pH-dependent optical responses.

For sensing layers prepared from deposition of inorganic-oxide based sensing layers such as silica particles on a substrate or an optic fiber and without being bound by theory, the optical response is thought to be associated with the effective refractive index modulation of the inorganic based sensing layers because in these films, nanoparticle aggregation is no longer relevant. In general, inorganic oxide based nanoparticles affixed to a substrate such that they do not exhibit a significant modification to interparticle spacing as a result of pH variation of the surrounding solution phase are preferred. In a particular embodiment, the inorganic-oxide nanoparticles fixed to the substrate exhibit a variation in interparticle spacing less than 10% over a pH range from 2.0 to 12.0. In an additional embodiment, the variation in interparticle spacing is less than 1% over a pH range from 2.0 to 12.0. Generally speaking, the optically active inorganic oxide-based nanoparticles display some degree of light absorption and/or scattering which is a required aspect of their useful application for the pH sensing application. In a particular embodiment, an individual optically active nanoparticle in the plurality of optically active nanoparticles has an extinction cross-section of at least $10^{-16}$ cm$^2$ over a subset of the wavelength range of from about 200 nanometers to about 3500 nanometers. In a particular embodiment, the subset of the wavelength range encompasses a continuous span of at least 10 wavelengths, and in another embodiment, the subset includes a wavelength within the one or more wavelengths of the optical signal. In an additional embodiment, the optically active nanoparticles have an extinction cross-section of at least $10^{-16}$ cm$^2$ for at least one of the wavelengths represented within the optical signal. In another embodiment, the optically active nanoparticles display a localized surface plasmon resonance, as determined through methods known in the art. See e.g., Willets et al., "Localized Surface Plasmon Resonance Spectroscopy and Sensing," *Annu. Rev. Phys. Chem.* 58 (2007), among others. Further, the optically active nanoparticles are not limited to strictly spherical shapes, and may be comprised of shapes such as triangular prisms, disks, shells, wires, rods, and others. When such structures are present, the average particle diameter refers and is equivalent to an equivalent circular diameter (ECD), which connotes the diameter of a circle with area equal to that of the projection of the particle on a plane. See e.g., Xu et al, "Comparison of sizing small particles using different technologies," *Powder Technology* 132 (2003).

In some embodiments, plurality of optically active nanoparticles has an average nanoparticle diameter of less than about 100 nanometers. The average size of the optically active nanoparticles may be tailored in order to derive a desired response. For example, relatively large optically active nanoparticles approaching 100 nm in diameter are expected to strongly scatter light in the visible range while relatively small optically active nanoparticles less than approximately 10-20 nm are not. Tailoring the particle size can therefore affect the wavelength and optical response of a optically active nanoparticles extinction, absorption, and scattering cross-section. Tailoring of particle size may also be important for optimizing additional aspects such as the stability of the pH sensing material as well as the type, degree, and kinetics of a pH sensing response. In an embodiment, the average nanoparticle diameter is greater than about 2 nm. The ability to vary features of the sensing layers comprised of inorganic oxide based nanoparticles that impact the nature of the optical response to interrogating electromagnetic radiation such as (1) particle size, (2) particle spacing, (3) geometrical arrangement of particles, and (4) particle shape are inherent advantages of the proposed approach that greatly increase the ability to optimize the sensor material for a particular optical pH sensing application.

In a particular embodiment, the pH sensing materials are substantially absent of any common pH indicator dyes and they do not exhibit a characteristic pKa value when dispersed directly in solution. Generally speaking, organic dye based optical pH indicators are well known in the art. Such indicator dyes have been embedded within a sol-gel based matrix such as silica for pH sensing, but the mechanism is typically thought to result from direct protonation or deprotonation reactions with indicator molecules in response to changes in solution phase pH. For pH indicator dyes, a well-defined pKa value is commonly defined in the art as the pH at which the reaction substantially occurs, and the reaction is well-known to occur with an associated change in optical signal when the indicator is dispersed within a solution. If the particles are known to have a well-defined pKa, the reaction associated with the pKa that occurs in a plurality of optically active nanoparticles when dispersed in solution results in a relative change of less than about 5%, more preferably less than 1%, and most preferably less than 0.1% between a first signal $S_1$ in a solution with a certain pH and a second signal $S_2$ in a solution with a certain pH2, where the first signal $S_1$ and the second signal $S_2$ are both an optical parameter at a given wavelength, and the optical parameter is an absorption, a transmission, a reflection, a scattering, or combinations thereof. Here, the first signal $S_1$ results when the plurality of nanoparticles are in contact with a given aqueous solution with a $pH_1$, and the second signal $S_2$ results when the plurality of nanoparticles are in contact with the given aqueous solution with a $pH_2$, and the relative change is such that an absolute value of $(S_1-S_2)/S_n$ multiplied by 100 is less than or equal to 5, where $S_n$ is the greater of either $S_1$ or $S_2$. In another particular embodiment, the $pH_1$ of the given aqueous solution is at least 3 pH units below the pKa of the nanoparticles at 25° C. and the $pH_2$ of the given aqueous solution is at least 3 pH units above the pKa of the nanoparticles at 25° C. In another embodiment, the given wavelength is one of the one or more wavelengths of the optical signal, and in a further embodiment the optical parameter is an absorption. In yet another embodiment, the given wavelength is one of the one or more wavelengths of the optical signal, and in a further embodiment the optical parameter is a scattering.

Within this disclosure, "optical signal" means a comparison of light incident on the pH sensing material and light exiting the pH sensing material at one or more wavelengths using optical spectroscopy. Correspondingly, the optical signal may reflect one specific wavelength, or may reflect a monitored band of wavelengths. The optical signal may be expressed as, for example, a transmittance at the one or more wavelengths, an absorption at the one or more wavelengths, or any other parameters which indicate the absorption, transmission, reflection, scattering or other optical impacts on the incident light as a result of interaction with the pH sensing material. As is understood, optical spectroscopy based on a comparison of the incident light and the exiting light may indicate the absorption, transmission, reflection, scattering, and optical impacts which occur as a result of interaction between the incident light and the pH sensing material. See e.g., Ingle, James D., and Stanley R. Crouch, *Spectrochemical analysis*, Englewood Cliffs, N.J.: Prentice Hall, 1988; see also Sole, Jose, *An Introduction to the Optical Spectroscopy of Inorganic Solids* (2005); see also Sarid, Dror and Challener, William, *Modern Introduction to Surface Plasmons: Theory, Mathematica Modeling, and Applications* (2010), among others. Additionally, the optical signal as disclosed here is generally not constrained to a specific wavelength or band of wavelengths. For example, the optical signal may occur at one or more wavelengths typically considered to be ultraviolet, visible, or near-infrared as those terms are used in the art, as well as wavelengths falling outside those delineated ranges.

As discussed, the optical signal as disclosed here is generally not constrained to a specific wavelength or band of wavelengths, and may reflect behavior at one specific wavelength or a monitored band of wavelengths. In some embodiments, the optical signal may exhibit a maxima or minima peak within a band of wavelengths, and it may be advantageous to evaluate an optical signal at or around the wavelength where the maxima or minima substantially occurs. For example the relative minima at $\lambda_P$ between wavelengths $\lambda_L$ and $\lambda_H$. However, the exhibition of a maxima or minima peak within a monitored band of wavelengths is not a requirement within this method, and the optical signal is not limited to wavelengths associated with relative maxima or minima. Within this disclosure and as discussed, optical signal may be monitored at any wavelength or over multiple wavelengths in a band of wavelengths.

Additionally, it is understood that when the disclosure describes monitoring an optical signal and thereby evaluating the pH of an aqueous solution, this includes operations where a shift in the optical signal serves as an indication of a shift in the pH of the aqueous solution. A "shift in the optical signal" means a variation between an initial optical signal and a subsequent optical signal at one or more wavelengths, where the initial optical signal is generated at a first time and the subsequent optical signal is generated at a second time, and where both the initial optical signal and the subsequent optical signal are generated by illuminating the pH sensing material with the light source emitting the incident light, collecting the exiting light, and comparing the incident light and the exiting light using optical spectroscopy. The shift in the optical signal may be recognized by detecting a variation between optical signals at any monitored wavelength or by variations at multiple wavelengths over a band of wavelengths. For example, the variation may be detected by monitoring a transmittance at a specific wavelength, the specific wavelength of an optical signal edge within a specified wave length range, the wavelength of an optical signal local maxima, a variation in the optical signal breadth, a variation in the optical signal amplitude, a variation in the optical signal full width at half maximum (FWHM), or any other techniques which may serve to indicate a variation between the initial optical signal and a subsequent optical signal. In an embodiment, the shift in the optical signal means a variation of at least 0.1% between an initial time-averaged optical signal and a subsequent time-averaged optical signal in transmittance, absorbance, or reflectance at a specific wavelength.

Figure 5:
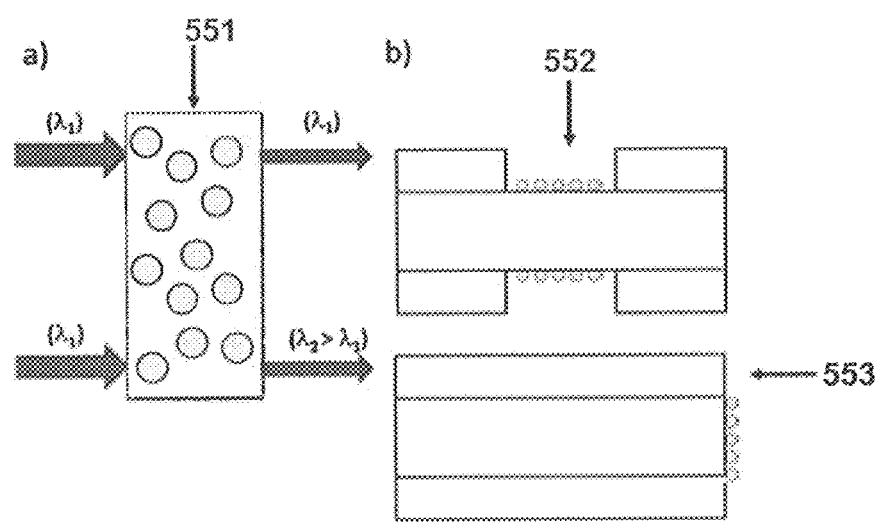
FIGS. 5(a)-(b) illustrate transmitted, fluoresced, and reflected transmission of an exiting optical signal.

Further, instruments performing the invented method may operate by measuring transmitted, fluoresced, and reflected transmission of an optical signal, as illustrated in FIG. 5. In FIG. 5a, where pH sensing materials are dispersed in a matrix 551, an optical transmitted signal is detected and measured. In the embodiment of a doped-inorganic oxide where fluorescence may result via the dopent, the fluorescence is detected and measured. As in FIG. 5b, both transmission 552 and reflection probes 553 are contemplated where the pH sensing material is incorporated onto a waveguide sensor.

Figure 6:
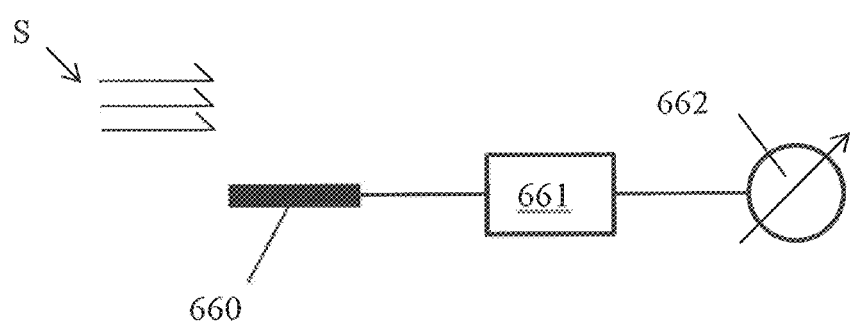
FIG. 6 illustrates an instrument using an embodiment of the pH sensing material.

In a particular embodiment, the pH sensing material is employed in an instrument such as that illustrated at FIG. 6. In this embodiment, the pH sensing material of this disclosure comprises a sensing head 660 in contact with an aqueous solution S. An interrogator 661 illuminates the pH sensing material comprising sensing head 660 with incident light and gathers exiting light. Interrogator 661 compares the incident light and the exiting light and generates a measurand, where the measurand is proportional to the optical signal as defined herein. Such interrogators for use in optical systems are known in the art. See e.g., Lee et al., "Review of the present status of optical fiber sensors," *Optical Fiber Technology* 9 (2003), and associated references. Interrogator 661 is in data communication with meter 662 which provides an indication of the magnitude of the measurand generated and communicated by interrogator 661. In this embodiment, the steps of illuminating the pH sensing material, collecting exiting light, and monitoring an optical signal based on a comparison of the incident light and the exiting light is conducted by interrogator 661, and monitoring the optical signal is conducted through observation of meter 662. An indication of the pH of aqueous solution S is provided by comparison of the observed meter reading and a reference meter reading, where the reference meter reading results from a reference measurand generated under reference conditions, such as when aqueous solution S has a neutral pH or some other condition.

EXAMPLES

Silica Based Fixed Optically Active Nanoparticles

Figure 7:
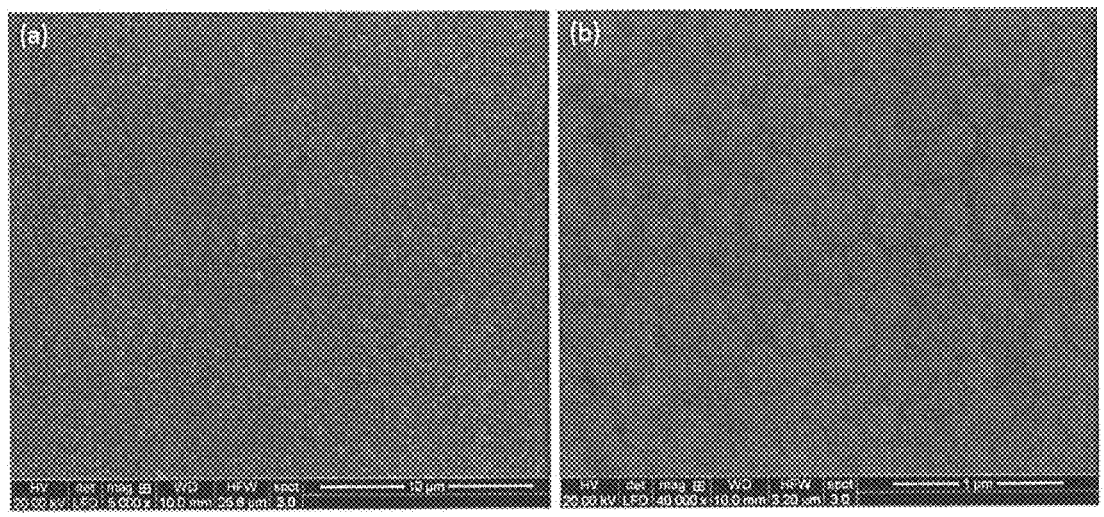
FIGS. 7(a)-(b) show an SEM image of silica based pH sensing material coated on a planar surface.
Figure 8:
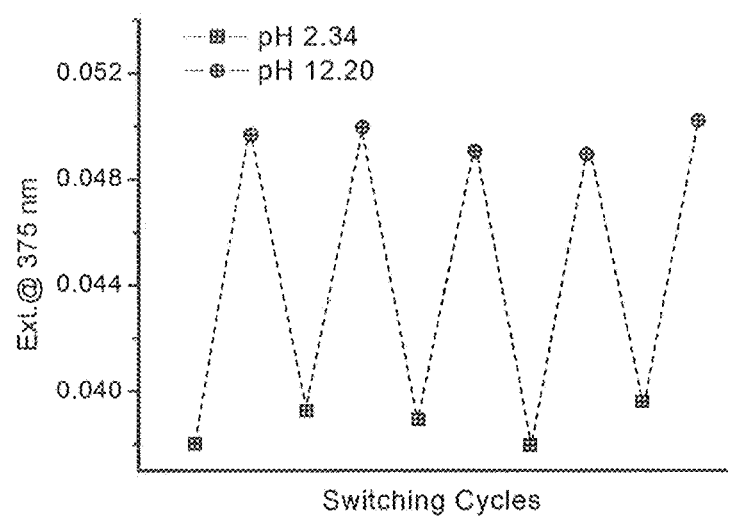
FIG. 8 illustrates the pH sensing material demonstrating light extinction across a pH range and multiple cycles.

Thick silica films were prepared by the deposition of silica particles was studied. These films were formed by deposition of silica nanoparticles on planar glass substrates through drop-coating and calcination at 473 K for 1 h to immobilize the particles with sufficient adhesion to the underlying substrate. As characterized by scanning electron microscopy (SEM), the final films have very rough surfaces which make them highly scattering (FIG. 7). The UV-Vis spectra of the roughened silica films at different pH values were recorded by placing the films into a sample cuvette containing buffer solutions. The light extinction of the roughened silica films indicated strong scattering dependent on the environmental pH which is not affected by complicating effects of aggregation and de-aggregation seen in silica colloids in solution due to the particles being affixed to the substrate and hence the interparticle spacing being essentially fixed. (FIG. 7) The pronounced optical response in basic pH ranges is a result of large variation in the effective refractive index of the silica films from the formation of the electrical double layer on the charged surface. The surface charging behavior and hence the pH dependent response can be modified for a particular desired pH dependence through selection of the identity of the inorganic oxide based nanoparticle as well as functionalization of the oxide based nanoparticle surface. Roughened silica based films prepared through deposition of silica nanoparticles on the substrate surface allow for simple and direct demonstrations of the reversibility of pH-controlled scattering behavior. However the same basic response is expected for alternative compositions of inorganic oxide based nanoparticles deposited on the surface. By placing roughened silica films prepared in this way alternatingly into buffer solutions at pH 2.34 and 12.20, the attenuation and amplification of light scattering from the silica nanoparticle based films was demonstrated to operate reversibly in multiple cycles (FIG. 8).

Metal-Inorganic Oxide/Core-Shell Suspended Optically Active Nanoparticles

Figure 9:
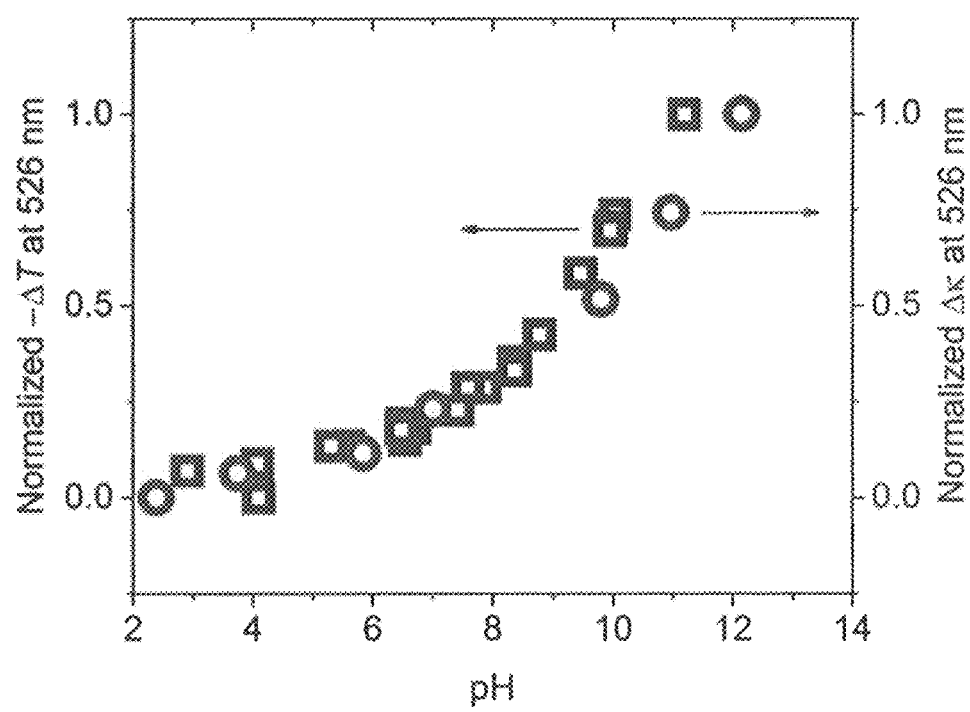
FIG. 9 illustrates light extinction across a pH range using an embodiment of the pH sensing material.

Metal-inorganic oxide/core-shell nanoparticles of gold embedded in a silica matrix were synthesized. 4 ml gold colloids in water solution (20 nm in diameter, $7\times10^{11}$ particles/ml) (BBI Solutions) were added to 20 ml 2-propanol. 0.5 mL ammonia solution (ACS reagent, 28 to 30%) and different amounts of TEOS (5 µl) to achieve the desired shell thicknesses were subsequently added to the reaction mixture under vigorous stirring. The reaction was allowed to proceed for 1 h at room temperature. The resulting mixture was centrifuged and rinsed with water. The cleaned Au@SiO2 core-shell nanoparticles were then kept in water at 4° C. The nanoparticles were characterized by an Agilent 8453 UV/vis spectrometer and transmission electron microscopy (TEM) using a JEOL 2000 operating at 200 kV in conventional bright field imaging mode. TEM images of the particles deposited on carbon TEM grids are illustrated in FIG. 4 along with the measured optical extinction spectrum as a function of pH of the solution. A monotonically enhanced extinction is observed with increasing solution phase pH. In addition to the expected localized surface plasmon absorption peak of the Au nanoparticles, a monotonically increasing scattering contribution is observed with decreasing wavelength. It appears that this scattering contribution is highly dependent upon solution phase pH. The estimated extinction for the particles (shown as squares) is plotted in FIG. 9 as a function of pH along with corresponding results plotted for a previously investigated Au/TEOS (shown as circles) thin film coated optical fiber sensor. The correspondence between the observed dependences is also strikingly similar to the well-known pH dependence of the surface charging of silica surfaces in solutions. See e.g. Wang et al., "Novel silica surface charge density mediated control of the optical properties of embedded optically active materials and its application for fiber optic pH sensing at elevated temperatures," *Nanoscale*, 2015, 7, 2527-2535, incorporated herein by reference. By affixing metal-inorganic oxide/core-shell nanoparticles of gold embedded in a silica matrix onto a substrate or optical waveguide structure, the nanoparticles can be used to create a pH dependent sensing layer that can be monitored through optical methods as described above.

Silica Based Optically Active Nanoparticles Fixed to a Silica Optical Fiber

Figure 10:
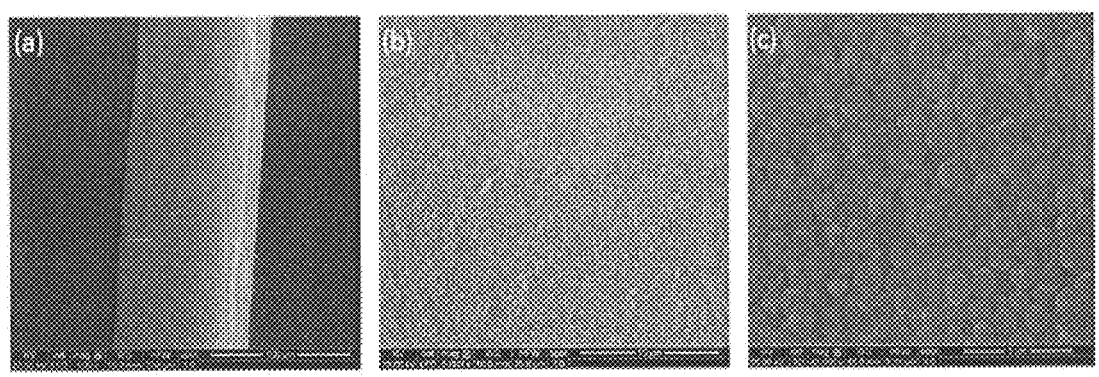
FIGS. 10(a)-(c) are SEM image of silica based pH sensing material coated on an optical fiber, at 100 μm, 10 μm, and 1 μm scale bar magnifications.
Figure 11:
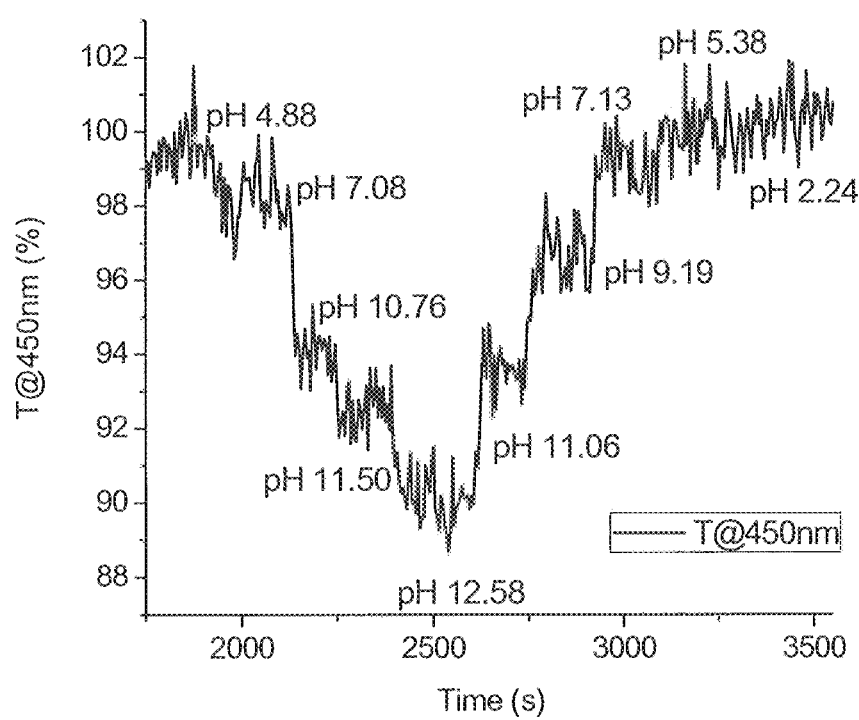
FIG. 11 illustrates pH sensing responses for a sensor at an interrogation wavelength of 450 nm.

Silica based pH sensing nanoparticle materials were deposited onto an optical fiber core through dip coating and curing at 476 K to immobilize the particles with sufficient adhesion to the underlying substrate. (See e.g. Wang et al.) As characterized by scanning electron microscopy (SEM) shown in FIG. 10, the final films have very rough surfaces which make them highly scattering. The resulting coated optical fiber was characterized by transmission spectra at different pH values of buffer solutions (FIG. 11). The monitored light extinction of the coated optical fibers confirmed the strong scattering dependence on the environmental pH. Corresponding optical fibers prepared without the inorganic oxide-based sensing layer deposited on the exposed core do not show a measurable sensing response which indicates the importance of the optically active inorganic oxide based nanoparticle sensing layer as the pH sensing material.

Thus, provided here is a method for evaluating the pH of an aqueous solution using a pH sensing material which generates an optical signal reflecting the pH. The pH sensing material is comprised of a plurality of inorganic oxide-based optically active nanoparticles, where the inorganic oxide-based optically active nanoparticles have a localized refractive index modulation over a pH range from 2.0 to 12.0 of at least 1%. The pH sensing material is fixed to a substrate, and the optically active nanoparticles demonstrate less than 10% change in interparticle spacing. The method generally comprises contacting the pH sensing material and the aqueous solution, illuminating the pH sensitive material with a light source, and generating an optical signal by comparing incident light and exiting light. The optical signal of the pH sensitive material varies in response to the pH of the aqueous solution, providing a means by which the pH and any changes in the pH may be analyzed.

It is to be understood that the above-described arrangements are only illustrative of the application of the principles of the present invention and it is not intended to be exhaustive or limit the invention to the precise form disclosed. Numerous modifications and alternative arrangements may be devised by those skilled in the art in light of the above teachings without departing from the spirit and scope of the present invention. It is intended that the scope of the invention be defined by the claims appended hereto.

In addition, the previously described versions of the present invention have many advantages, including but not limited to those described above. However, the invention does not require that all advantages and aspects be incorporated into every embodiment of the present invention.

All publications and patent documents cited in this application are incorporated by reference in their entirety for all purposes to the same extent as if each individual publication or patent document were so individually denoted.

We claim:

1. A method of evaluating a pH of an aqueous solution comprising:
   contacting a pH sensing material with the aqueous solution, where the pH sensing material comprises:
   a plurality of optically active nanoparticles fixed to a substrate, where the plurality of optically active nanoparticles are an inorganic metal oxide, wherein one or more of the optically active nanoparticles in the plurality of optically active nanoparticles has a localized refractive index modulation over a pH range from 2.0 to 12.0 of at least 1% and, where the plurality of optically active nanoparticles have an average nanoparticle diameter of less than about 500 nanometer;
   illuminating the pH sensing material with a light source emitting incident light;
   collecting exiting light, where the exiting light is light that originates at the light source and is transmitted, reflected, scattered or a combination thereof by the pH sensing material; and
   monitoring an optical signal based on a comparison of the incident light and the exiting light using optical spectroscopy, thereby evaluating the pH of the aqueous solution.

2. The method of claim 1 where the substrate is a silica substrate.

3. The method of claim 1 where the substrate is a waveguide.

4. The method of claim 1 where the pH sensing material is fixed to the substrate by a matrix material, where the matrix material is substantially transparent to incident light and exiting light.

5. The method of claim 4 where the matrix material is an ion-selective filtering matrix material.

6. The method of claim 1 where pH sensing material is fixed directly to the substrate, and where the pH sensing material is overcoated by an ion-selective filtering overcoat.

7. The method of claim 1 where the optically active nanoparticles are silica.

8. The method of claim 1 where the optically active nanoparticles are electronically conductive inorganic metal oxides.

9. The method of claim 8 where the electronically conductive inorganic metal oxides are Al-doped ZnO, Sn-doped In2O3, or Nb-doped Ti02.

10. The method of claim 1 where the optically active nanoparticles exhibit a variation in interparticle spacing less than 10% over a pH range from 2.0 to 12.0.

11. The method of evaluating the pH of the aqueous solution of claim 1, further comprising:
    emitting incident light using an interrogator in optical communication with the pH sensing material and illuminating the pH sensing material, and gathering exiting light using the interrogator in optical communication with the pH sensing material, and monitoring the optical signal based on the comparison of the incident light and the exiting light with optical spectroscopy using the interrogator, thereby illuminating the pH sensing material with the light source emitting incident light, collecting exiting light, and monitoring the optical signal based on the comparison of the incident light and the exiting light using optical spectroscopy;
    generating a measurand using the interrogator based on the optical signal, and communicating the measurand to a meter in data communication with the interrogator; and
    receiving the measurand at the meter and displaying a meter reading on the meter based on the measurand.

12. A method of evaluating a pH of an aqueous solution comprising:
    contacting a pH sensing material with the aqueous solution, where the pH sensing material comprises:
    a plurality of optically active nanoparticles, wherein the plurality of optically active nanoparticles are metal-inorganic oxide/core-shell nanoparticles comprising a metal core and inorganic oxide shell, wherein one or more of the optically active nanoparticles in the plurality of optically active nanoparticles has a localized refractive index modulation over a pH range from 2.0 to 12.0 of at least 1% and, where the plurality of optically active nanoparticles have an average nanoparticle diameter of less than about 500 nanometer;

illuminating the pH sensing material with a light source emitting incident light; collecting exiting light, where the exiting light is light that originates at the light source and is transmitted, reflected, scattered or a combination thereof by the pH sensing material; and monitoring an optical signal based on a comparison of the incident light and the exiting light using optical spectroscopy, thereby evaluating the pH of the aqueous solution.

13. The method of claim 12 where the pH sensing material is fixed to a silica substrate.

14. The method of claim 13 where the substrate is a waveguide.

15. The method of claim 13 where the pH sensing material is fixed to the substrate by a matrix material, where the matrix material is substantially transparent to incident light and exiting light.

16. The method of claim 15 where the matrix material is an ion-selective filtering matrix material.

17. The method of claim 13 where the pH sensing material is fixed directly to the substrate, and where the pH sensing material is overcoated by an ion-selective filtering overcoat.

18. The method of claim 12 where the metal is gold, palladium, silver, platinum, ruthenium, rhodium, osmium, or iridium.

19. The method of claim 12 where the inorganic oxide comprises silica.

20. The method of claim 12 where the optically active nanoparticles exhibit a variation in interparticle spacing less than 10% over a pH range from 2.0 to 12.0.

21. The method of evaluating the pH of the aqueous solution of claim 12, further comprising: emitting incident light using an interrogator in optical communication with the pH sensing material and illuminating the pH sensing material, and gathering exiting light using the interrogator in optical communication with the pH sensing material, and monitoring the optical signal based on the comparison of the incident light and the exiting light with optical spectroscopy using the interrogator, thereby illuminating the pH sensing material with the light source emitting incident light, collecting exiting light, and monitoring the optical signal based on the comparison of the incident light and the exiting light using optical spectroscopy;

generating a measurand using the interrogator based on the optical signal, and communicating the measurand to a meter in data communication with the interrogator; and receiving the measurand at the meter and displaying a meter reading on the meter based on the measurand.

* * * * *